United States Patent
Kikuchi et al.

(10) Patent No.: US 7,060,496 B2
(45) Date of Patent: Jun. 13, 2006

(54) CULTURE MEDIUM FOR IN VITRO CULTURE OF IN VITRO-PRODUCED PORCINE EMBRYO AND METHOD FOR IN VITRO PRODUCTION OF PORCINE EMBRYO USING THE CULTURE MEDIUM

(75) Inventors: Kazuhiro Kikuchi, Tsukuba (JP); Hiroyuki Kaneko, Tsukuba (JP); Junko Noguchi, Ushiku (JP)

(73) Assignee: National Institute of Agrobiological Sciences, Tsukuba (JP)

( * ) Notice: Subject to any disclaimer, the term of this patent is extended or adjusted under 35 U.S.C. 154(b) by 0 days.

(21) Appl. No.: 10/790,113

(22) Filed: Mar. 2, 2004

(65) Prior Publication Data

US 2004/0166578 A1 Aug. 26, 2004

Related U.S. Application Data

(62) Division of application No. 10/061,321, filed on Feb. 4, 2002, now Pat. No. 6,743,629.

(30) Foreign Application Priority Data

Sep. 26, 2001 (JP) ............................. 2001-292814

(51) Int. Cl.
*C12N 5/06* (2006.01)
*C12N 5/00* (2006.01)

(52) U.S. Cl. ...................... 435/404; 435/408; 435/383; 435/391

(58) Field of Classification Search ................ 435/404, 435/408, 383, 391
See application file for complete search history.

(56) References Cited

U.S. PATENT DOCUMENTS 5,213,979 A 5/1993 First et al.
5,972,592 A * 10/1999 Suarez .......................... 435/2

FOREIGN PATENT DOCUMENTS

EP 0 345 082 6/1989

OTHER PUBLICATIONS

Kaoru Suzuku et al. Proc. 93rd Annual Meeting of Japanese Society of Animal Reproduction. 2000, p. 68.*

R. Marchal, et al. "Developmental Competence of Prepubertal and Adult Swine Oocytes: Birth of Piglets from In Virto-Produced Blastocysts", An International Journal of Animal Reproduction—Proceedings of the Annual Converence International Embryo Transfer Society Maastricht, vol. 53, No. 1, Jan. 1, 2000, p. 361.

M. Mattioli, et al., "Developmental Competence of Pig Oocytes Matured and Fertilizer In Vitro", THERIOGENOLOGY, vol. 31, No. 6, Jun. 1989, pp. 1201-1207.

R.M. Petters, et al., "Addition of Taurine or Hypotaurine to Culture Medium Improves Development of One-and Two-Cell Pig Embroys In Vitro", THERIOGENOLOGY, vol. 35, No. 1, Jan. 1991, p. 253.

Kazuhiro Kikuchi, et al., "Developmental Competence, After Transfer to Recipients, of Porcine Oocytes Matured, Fertilized, and Cultured In Vitro", Biology of Reproduction, 60, 1999, pp. 336-340.

R.M. Petters, et al., "Culture of Pig Embryos", Journal of Reproduction and Fertility Supplement, 48, 1993, pp. 61-73.

Gandhi, et al., Molecular Reproduction and Development, 2001. vol. 58, No. 3, pp. 269-275.

Barnes, et al. Human Reproduction, 1995, vol. 10, No. 12, pp. 3243-3247.

Gardner D. Theriogenology, 1998, 49:83-102.

* cited by examiner

*Primary Examiner*—Vera Afremova
(74) *Attorney, Agent, or Firm*—Oblon, Spivak, McClelland, Maier & Neustadt, P.C.

(57) ABSTRACT

The invention provides an in vitro culture medium for in vitro-produced porcine embryo for the in vitro culture thereof, which can improve the quality of the resulting blastocyst and can raise the ratio of the development into fetus and infant after transfer, along with a method for in vitro culturing in vitro-produced porcine embryo using the culture medium, which can improve the quality of the resulting blastocyst and can develop the blastocyst into fetus and infant after transfer.

A culture medium for the in vitro culture of in vitro-produced porcine embryo, which contains lactic acid and pyruvic acid; a culture medium for the in vitro culture, which is conditioned with oviductal epithelial cell; and a method for in vitro culturing in vitro-produced porcine embryo, comprising culturing the in vitro-produced porcine embryo using the culture medium for the 0 to 2-day term after fertilization and subsequently culturing the embryo in a glucose-containing culture medium.

2 Claims, No Drawings

CULTURE MEDIUM FOR IN VITRO CULTURE OF IN VITRO-PRODUCED PORCINE EMBRYO AND METHOD FOR IN VITRO PRODUCTION OF PORCINE EMBRYO USING THE CULTURE MEDIUM

CROSS-REFERENCE TO RELATED APPLICATIONS

The present application is a divisional application of U.S. application Ser. No. 10/061,321 filed Feb. 4, 2002, U.S. Pat. No. 6,743,629.

FIELD OF THE INVENTION

The present invention relates to a culture medium for the in vitro culture of porcine embryo which is produced in vitro (this culture medium will be referred as in vitro culture medium) and a method for in vitro production of porcine embryo using the said culture medium. More specifically, the invention relates to a culture medium for the in vitro culture of porcine embryo which is produced in vitro (this porcine embryo will be referred as in vitro-produced porcine embryo hereinafter), which can improve the quality of the resulting blastocyst and can also increase the development ratio into fetus and infant (or piglet) after transfer of the blastocyst, and a method for in vitro production of porcine embryo using the culture medium.

BACKGROUND OF THE INVENTION

In vitro maturation and in vitro fertilization oocyte (in vitro-produced embryo) has been used recently for the purpose of breeding and growing superior species in mammals. Additionally, the technique for in vitro producing embryo has also been utilized for the production of transgenic animals or clone animals.

In vitro-produced embryo can be generated for porcine [Theriogenology, Vol. 31, p. 1201–1207, 1989], but the resulting blastocyst is poor in quality, with the total cell number of about 35, which is extremely less compared with that of the in vivo-derived blastocyst at the same stage (total cell number of about 60 to 165).

First success has been attained in the production of piglet, more recently, by transferring a blastocyst to a female pig recipient [Theriogenology, Vol. 53, p. 361, 2000]. However, the number of piglets produced is only one to two, inefficiently. The reason why the technique cannot make a progress may possibly reside in the immaturity of the technique for the in vitro culture of in vitro-produced embryo.

According to the last report by some of the present inventors [Biology of Reproduction, Vol. 60, p. 336–340, 1999], it was verified that the in vitro culture of in vitro-produced embryo for a term as short as one or two days deteriorated the development ratio into fetus and infant after transfer.

For culturing in vitro-produced porcine embryo, the NCSU culture medium [Journal of Reproduction and Fertility Supplement, Vol. 48, p. 61–73, 1993] has been used widely. The culture medium contains glucose as an energy source. Glucose is a great energy source, but a possibility is suggested that the metabolites in the form of peroxide might potentially affect the culturing cell adversely. In embryo, in particular, the metabolites cause a concern of adverse effects on the gene expression and the cell cycle progress.

In such circumstances, it is desired to improve the in vitro culture technique of in vitro-produced porcine embryo.

SUMMARY OF THE INVENTION

An object of the invention is to provide a culture medium for the in vitro culture of in vitro-produced porcine embryo, which can improve the quality of the resulting blastocyst and can also increase the development ratio into fetus and piglet after transfer.

It is another object of the invention to provide a method for in vitro production of porcine embryo using the culture medium, thereby enabling to develop into high-quality blastocyst and also to develop into fetus or piglet after transferring of the blastocyst.

DETAILED DESCRIPTION OF THE INVENTION

So as to attain the objects, the inventors have made investigations and attempts to make a modification of the culture method of the two-day term in the early post-fertilization stage.

The reason why the two-day term in the early stage is targeted has a relation with the effect on the development ratio after transfer as described above and is due to the belief that the two-day term, in case of pig, corresponds to the preliminary stage for the expression of genes intrinsic to embryo, namely the 4-cell stage where the development is found to be arrested. In other words, the inventors have expectantly anticipated that the optimization of the culture method during the term can sufficiently progress subsequent development.

Thus, the inventors have determined to use pyruvic acid and lactic acid as energy sources in place of glucose in the conventional NCSU culture medium. Consequently, the inventors have found that the use of such culture medium containing these substances may possibly improve the quality of the blastocyst recovered by the in vitro culture of in vitro-produced porcine embryo.

Post-fertilization embryo exists in the oviduct in living organisms for the early two days, namely up to the 4-cell stage. Accordingly, the inventors have made attempts to develop a culture method mimicking the environment in the oviduct. The inventors have therefore focused their attention to oviductal epithelium. Oviduct epithelium secretes various factors participated in the cell growth and additionally adjusts the ions in a culture medium owing to the action of the cell itself. Hence, it is believed with higher possibility that so-called oviductal epithelial cell-conditioned culture medium containing oviductal epithelial cells at a dispersed state in the medium mimics in vitro the environment in oviduct, to support the early development.

By transferring the blastocyst recovered from the improved in vitro culture broth into a female pig recipient, finally, the inventors have verified that the developmental competence and transfer efficiency of the embryo has been improved significantly.

The present invention has been achieved, based on these findings.

A first aspect of the present invention relates to a culture medium for the in vitro culture of in vitro-produced porcine embryo, comprises containing lactic acid and pyruvic acid.

A second aspect of the present invention relates to a culture medium for the in vitro culture wherein the culture medium is conditioned with oviductal epithelial cell.

A third aspect of the present invention relates to a method for in vitro culturing of in vitro-produced porcine embryo, comprising culturing an in vitro-produced porcine embryo in the culture medium of the first or second aspect of the invention for 0 to 2 days after fertilization, and subsequently culturing the embryo in a glucose-containing culture medium.

The culture medium for the in vitro culture of the first aspect of the invention will now be described below.

A characteristic of the culture medium is basically comprises the NCSU culture medium, for example NCSU37, from which glucose is preliminarily removed and to which lactic acid and pyruvic acid are added in place of glucose.

The reference [Journal of Reproduction and Fertility Supplement, Vol. 48, p. 61–73, 1993] discloses about the NCSU culture medium and other culture medium for porcine embryo. For general porcine embryo culture, NCSU23 and NCSU37 are used. For culturing in vitro-produced porcine embryo, in particular, these culture medium as well as the M-199 culture medium and the SOF culture medium are used.

Further, sucrose can be used in place of sorbitol used in NCSU37, while taurine and hypotaurine used in NCSU23 can also be used in place of sorbitol.

Salts of lactic acid are used as lactic acid, including for example alkali metal salts such as sodium salt and potassium salt and alkali earth metal salts such as calcium salt. These may be used singly or in combination of two or more thereof.

The content of lactic acid in the culture medium is generally 0.25 to 5.5 μL/mL, preferably about 0.40 to 1.5 μL/mL in 60% solution.

As pyruvic acid, further, preference is given to pyruvate salts, particularly sodium pyruvate.

The content of pyruvic acid in the culture medium is 0.009 to 0.036 mg/mL, preferably about 0.010 to 0.025 mg/mL.

As described in the second aspect of the present invention, the culture medium being conditioned with an oviductal epithelial cell is preferably used as the culture medium for the in vitro culture. Specifically, the culture medium contains oviductal epithelial cells at a dispersed state. Thus, the culture medium is referred to as "oviductal epithelial cell-conditioned medium".

Oviductal epithelium secretes various factors responsible for the cell growth and additionally adjusts the ions in a culture medium owing to the action of the cell itself. Hence, so-called oviductal epithelial cell-conditioned medium containing oviductal epithelial cells at a dispersed state in the medium can mimic the environment in oviduct to support the early development.

Oviductal epithelial cells collected from various tissues of living organisms can be used as the oviductal epithelial cell. Particularly, an oviductal epithelial cell obtained from the same porcine species as that of the embryo which is subjected to the cultivation is preferably used.

The oviductal epithelial cell-conditioned medium can be prepared for example by the method described in the Proceedings of the Japanese Society of Animal Reproduction, p. 68, 2000. More specifically, oviductal epithelial cell is added at $1$–$10\times10^6$ cells/mL to a basal culture medium containing lactic acid and pyruvic acid, and the resulting mixture is cultured for 2 days. Subsequently, the culture broth is centrifuged if necessary to recover the supernatant, to which is then added an approximately equal volume of the basal culture medium. In such manner, the conditioned-medium can be prepared. NCSU 37 and a modified NCSU37 prepared by replacing glucose in NCSU37 with pyruvic acid and lactic acid are appropriate as the basal culture medium.

Additionally, examples of carrier protein and the like are, besides serum albumin and serum, polyvinyl alcohol and polyvinylpyrrolidone. A reducing substance includes for example 2-mercaptoethanol (beta-mercaptoethanol), dithiothreitol and glutathione of reduced type.

Furthermore, antibiotics such as penicillin, streptomycin, gentamycin and erythromycin as well as antifungal agents such as amphotericin B and nystatin may appropriately be added to the culture medium of the invention.

The culture medium for the in vitro culture in accordance with the present invention may be mixed, if necessary, with known equilibrium salt solutions such as Tyrode's solution, Krebs-Ringer bicarbonate salt solution, Earl's solution, Hanks' solution, Dulbecco-phosphate buffer or modified solutions thereof; known culture medium such as 199 medium, MEM medium, Waymouth medium, Ham's medium, Brinster's medium (BMOC), m-Tyrode's mediums, BWW medium, Whitten medium, TYH medium, m-KRB medium, CZB medium, TLH medium, SOF medium, and BECM medium [see Journal of Reproduction and Fertility Supplement, Vol. 48, p. 61–73, 1993]; or modified culture media thereof, for use.

As described above, the essential composition of the culture medium for the in vitro culture for use in accordance with the present invention preferably comprises those of the NCSU culture medium, from which glucose is preliminarily removed. The NCSU culture medium includes for example NCSU37 culture medium [Journal of Reproduction and Fertility Supplement, Vol. 48, p. 61–73, 1993] and NCSU23 culture medium [Petters, R. M., Reed M. L., Theriogenology, 1991; 35, 253 (Abstract)]. NCSU37 culture medium is particularly preferable.

A preparation of the culture medium for the in vitro culture in accordance with the present invention is generally in a liquid form, but the culture medium may optionally be in the form of solid or semi-solid to meet a need.

The in vitro-produced porcine embryo to be cultured using the culture medium for the in vitro culture in accordance with the present invention is an embryo (fertilized oocyte) prepared by the in vitro maturation and in vitro fertilization of an oocyte collected from porcine ovary according to ordinary method.

The in vitro maturation is done generally in the NCSU culture medium [Journal of Reproduction and Fertility Supplement, Vol. 48, p. 61–73, 1993], with no specific limitation. Hence, the 199 medium, Waymouth medium, MEM medium and the like may also be used, satisfactorily.

The in vitro fertilization can be done according to general methods. For example, the in vitro fertilization can be proceeded by the in vitro fertilization of an embryo with an epididymis sperm frozen and thawed by an appropriate method.

The culture medium for the in vitro culture in accordance with the present invention can preferably be used for the in vitro culture of in vitro-produced porcine embryo. The method for the in vitro culture in the third aspect of the present invention is pertaining to the in vitro culture of in vitro-produced porcine embryo using the culture medium for the in vitro culture.

As described above, in vitro-produced porcine embryo is an embryo (fertilized oocyte) prepared by in vitro maturation and in vitro fertilization of an oocyte collected from porcine ovary according to general methods.

The in vitro culture method of the invention comprises culturing an in vitro-produced porcine embryo in the culture medium for 0 to 2 days after fertilization and subsequently culturing the embryo in the glucose-containing culture medium.

The in vitro culture requires culturing in vitro-produced porcine embryo for 0 to 2 days, namely up to the 4-cell stage, and so as to progress subsequent development sufficiently, importantly, the culture during the term should be carried out appropriately.

From the standpoint of the prevention against embryo damage, generally, the cultivation condition during the term is preferably as follows: a temperature of 37 to 40° C. (about 38.5° C.) and a condition of 1–20% oxygen, 5% carbon dioxide and 75–94% nitrogen (for example, 5% oxygen, 5% carbon dioxide, and 90% nitrogen).

The cultivation in the glucose-containing culture medium is now described. As the culture medium, preference is given to the NCSU culture medium, for example NCSU37 culture medium. The cultivation in the glucose-containing culture medium is continued for 2 to 8 days, generally for 2 to 6 days after fertilization. The other cultivation conditions are the same as the above cultivation conditions for 0 to 2 days after fertilization.

The development status after the cultivation in combination of the two types of culture media in the manner as described above can be examined, for example, by fixing and staining all the embryos or oocytes after the completion of the culture and assaying the blastocyst development ratio and the total cell number.

According to the in vitro culture method in the third aspect of the present invention, a blastocyst with a larger total cell number and excellent quality can be obtained. By transferring the blastocyst into a female pig recipient, the ratio of subsequent development into fetus and piglet is highly increased.

The culture medium for the in vitro culture in accordance with the present invention can improve the quality of blastocyst obtained from the in vitro culture of in vitro-produced porcine embryo and can raise the ratio of the development into fetus and infant after transfer.

In accordance with the in vitro culture method of the present invention, further, the in vitro culture of in vitro-produced porcine embryo in the culture medium enables the development into blastocyst of high quality and the development into fetus and infant after transfer.

Accordingly, it is shown that the in vitro-produced blastocyst in the culture system provided in accordance with the present invention enables the development into infant after transfer.

The present invention can be believed to be a basic technique applicable for example to the reproduction engineering in porcine for transgenic animal or clone production.

EXAMPLES

The invention will now be described with reference to examples, but the invention is not limited to the examples.

Example 1

Using the culture medium based on the in vitro culture medium (NCSU37 culture medium), in vitro-produced porcine embryo was cultured in vitro, for comparison in terms of the development of the in vitro-produced embryo.

As shown in Table 1, first, a solution was prepared by removing glucose from the known NCSU37 culture medium and adding sodium pyruvate and sodium lactate (referred to as NCSU37-PyrLac hereinafter) instead, and the known glucose-containing NCSU37 culture medium (referred to as NCSU37-Glu hereinafter) was also prepared. These were used as in vitro culture media.

TABLE 1

(Compositions of in vitro culture media)

| Name | Constitutive component | NCSU37-PyrLac | NCSU37-Glu |
| --- | --- | --- | --- |
| NaCl | 3.971 g/500 ml | | |
| KCl | 0.223 g/500 ml | | |
| $CaCl_2.H_2O$ | 0.156 g/500 ml | | |
| Solution A | | 80 ml | 80 ml |
| $KH_2PO_4$ | 0.101 g/500 ml | | |
| $MgSO_4.H_2O$ | 0.183 g/500 ml | | |
| Glutamine | 0.091 g/500 ml | | |
| Phenol red | 1.0 mg/500 ml | | |
| Solution B | | 20 ml | 20 ml |
| $NaHCO_3$ | 5.265 g/500 ml | | |
| Phenol red | 1.0 mg/500 ml | | |
| Sorbitol | | 0.2186 g | 0.2186 g |
| Glucose | | — | 100 mg |
| Sodium pyruvate | | 1.8172 mg | — |
| Sodium lactate (60% solution) | | 51 μl | — |
| 2-Mercaptoethanol | | 390 mg | 390 mg |
| Bovine serum albumin | | 400 mg | 400 mg |
| Penicillin G | | 10,000 units | 10,000 units |
| Streptomycin | | 10 mg | 10 mg |

Immature porcine oocyte was cultured in a known maturation in vitro culture medium (10% follicular fluid-added NCSU37 culture medium), which was then subjected to in vitro fertilization with frozen-thawed epididymis sperm according to a conventional method. After fertilization, in vitro culture was done for 6 days.

The culture was performed in both an early two-day term (0 to 2 days after fertilization) and a late four-day term (2 to 6 days after fertilization), separately. As shown in Table 2, NCSU37-PyrLac and NCSU37-Glu in combinations were used as the culture media for the early term and the late term at experiments. For both the early term and the late term, the culture was performed under conditions of 38.5° C. and 5% oxygen, 5% $CO_2$, 90% nitrogen.

On day 6 after the start of the culture, all the embryos or oocytes were fixed and stained, to examine the developmental competence. The combinations of the culture media, the blastocyst development ratio and the total cell number of the resulting blastocyst are shown in Table 2. Further, the development ratio (in %) and the cell number (in cells) are shown in mean±standard error.

TABLE 2

Effects of combinations of in vitro culture media on the development of in vitro-produced porcine embryo

| In vitro culture medium combination | | Blastocyst | |
| --- | --- | --- | --- |
| On days 0 to 2 after fertilization | On days 2 to 6 after fertilization | development ratio (in %) | Total cell number (in cells) |
| NCSU37-Glu | NCSU37-Glu | 14.5 ± 5.3[bc] | 35.4 ± 1.9[b] |
| NCSU37-Glu | NCSU37-PyrLac | 5.8 ± 1.7[b] | 37.1 ± 3.3[b] |
| NCSU37-PyrLac | NCSU37-Glu | 25.3 ± 6.9[c] | 48.7 ± 2.3[c] |
| NCSU37-PyrLac | NCSU37-PyrLac | 18.1 ± 4.7[bc] | 37.1 ± 2.1[b] |

[b,c]significant difference between different signs ($p < 0.05$)

Table 2 apparently shows higher blastocyst development ratios when NCSU37-PyrLac was used as the culture medium on days 0 to 2 after fertilization, compared with the case when NCSU37-Glu was used. Particularly when the embryo was cultured in the NCSU37-PyrLac on days 0 to 2 after fertilization and in the NCSU37-Glu on days 2 to 6 after fertilization, apparently, the blastocyst development ratio is likely to be higher and the total cell number is also significantly higher, compared with the cases when the other combinations of the culture media were used.

This indicates that the use of the culture medium containing lactic acid and pyruvic acid in accordance with the present invention as the culture medium for use in the early two-day term of the in vitro culture (on days 0 to 2 after fertilization) highly efficiently yields blastocyst with a larger total cell number of the in vitro-produced embryo and with high quality.

Example 2

Oviductal epithelial cell-conditioned culture medium (referred to as CM hereinafter) was used as an in vitro culture medium, for in vitro culturing in vitro-produced porcine embryo to compare the blastocyst development.

The procedure for preparation of CM follows the previous report [the Proceedings of the Japanese Society of Animal Reproduction, p. 68, 2000]. More specifically, the basal culture medium was NCSU37-PyrLac, to which was added an equal volume of oviductal epithelial cell for culture. On day 2 after the start of the culture, the culture broth was centrifuged to recover the supernatant, which was designated CM.

For in vitro embryo culture, an equal volume of fresh NCSU37-PyrLac was added to CM, and the resulting culture medium was designated in vitro culture medium (referred to as NCSU37-PyrLac/CM hereinafter).

In vitro maturation and in vitro fertilization were performed in the same manner as in Example 1. Then, in vitro culture was progressed in the NCSU37-PyrLac or NCSU37-PyrLac/CM for the two-day term after fertilization and in the NCSU37-Glu for the subsequent four-day term.

On day 6 after the start of the culture, all embryos or oocytes were fixed and stained, to examine the developmental competence. Table 3 shows the combinations of the culture media, the blastocyst development ratio and the total cell number of blastocyst.

TABLE 3

Effects of combinations of in vitro culture media on the development of in vitro-produced porcine embryo

| In vitro culture medium combination | | Blastocyst | |
|---|---|---|---|
| On days 0 to 2 after fertilization | On days 2 to 6 after fertilization | development ratio (in %) | Total cell number (in cells) |
| NCSU37-PyrLac | NCSU37-Glu | 24.8 ± 2.1 | 48.4 ± 4.1[b] |
| NCSU37-PyrLac/ CM | NCSU37-Glu | 26.9 ± 3.2 | 58.3 ± 7.5[c] |

[b,c]significant difference between different signs (p < 0.05)

Table 3 indicates a slightly higher blastocyst development ratio and a significantly larger total cell number of blastocyst when the NCSU37-PyrLac/CM was used for the 0–2-day term after fertilization, together with the NCSU37-Glu for the 2–6-day term after fertilization, compared with the case when the NCSU37-PyrLac was used for the 0–2-day term after fertilization and the NCSU37-Glu was used for the 2–6-day term after fertilization (namely, the case of no use of the conditioned-medium).

This indicates that the use of the oviductal epithelial cell-conditioned medium of the present invention as the culture medium for the early 2-day term (on days 0 to 2 after fertilization) for the in vitro culture highly efficiently yields a high-quality blastocyst with a larger total cell number of the in vitro-produced embryo.

Example 3

As in vitro culture media, the NCSU37-PyrLac/CM was used for the early two-day term (on day 0 to day 2 after fertilization) while the NCSU37-Glu was used subsequently for the late 3- or 4-day term.

On days 5 and 6 after fertilization, blastocysts in progressed developmental stages (expansion-stage blastocyst and expanded blastocyst) were selected under stereomicroscopy.

The development ratio from embryo and the total cell number were assayed, and the results are shown in Table 4 (herein, the cell number was assayed after fixation and staining). The development ratio (in %) and the cell number (in cells) are shown in mean±standard error.

TABLE 4

Developmental stage of in vitro-produced porcine embryo cultured in culture medium in vitro

| In vitro culture term | Expansion-stage blastocyst | | Expanded blastocyst | |
|---|---|---|---|---|
| | Development ratio (in %) | Cell number (in cells) | Development ratio (in %) | Cell number (in cells) |
| On day 5 | 12.2 ± 1.2 | 49.7 ± 2.5 | — | — |
| On day 6 | 9.0 ± 3.0 | 42.4 ± 2.2 | 10.8 ± 0.2 | 80.2 ± 3.0 |

Table 4 shows that viable blastocysts (expansion-stage blastocyst and expanded blastocysts) which could be selected under stereomicroscopy were selected on days 5 and 6 after the start of culture. The cell number reveals that these blastocysts were in the sufficiently progressed developmental stages.

This indicates that the blastocyst obtained by culturing in vitro the in vitro-produced porcine embryo in the in vitro culture medium in accordance with the present invention can sufficiently progress the development on days 5 to 6 after fertilization.

Example 4

The expansion-stage blastocyst on day 5 of culture as obtained in Example 3 was transferred in one female porcine recipient, while the expanded blastocyst on day 6 of culture was transferred in two female porcine recipients. All the animals became pregnant. The former produced 8 living piglets and the latter produced 11 piglets in total. Herein, the number of transferred embryos per one animal was 50.

This apparently demonstrates that the transfer of the in vitro-produced porcine embryo which is preliminarily in vitro cultured up to blastocyst in the in vitro culture medium of the present invention can progress the development into fetus and piglet, with absolutely no deterioration of the development ratio after transfer.

What is claimed is:

1. An in vitro culture medium comprising NCSU37 culture medium from which glucose is removed and to which sodium lactate and sodium pyruvate are added, wherein the amount of sodium lactate is from 0.25 to 5.5 µg/ml of a 60% solution and the amount of sodium pyruvate is from 0.009 to 0.036 mg/ml.

2. The in vitro culture medium for the in vitro culture according to claim 1, which is conditioned with oviductal epithelial cells.

* * * * *